United States Patent [19]

Arya et al.

[11] Patent Number: 5,354,871

[45] Date of Patent: Oct. 11, 1994

[54] PYRROLINE N-OXIDE DERIVATIVES

[75] Inventors: Prabhat Arya, Gatineau; David Griller, Ottawa, both of Canada

[73] Assignee: National Research Council of Canada, Ottawa, Canada

[21] Appl. No.: 46,727

[22] Filed: Apr. 16, 1993

[30] Foreign Application Priority Data

Nov. 27, 1992 [CA] Canada ................................. 2083977

[51] Int. Cl.$^5$ .................. C07D 207/46; C07D 403/12; C07D 495/02
[52] U.S. Cl. ..................................... 548/542; 548/518; 548/303.7
[58] Field of Search ...................... 548/542, 303.7, 518

[56] References Cited

PUBLICATIONS

A. Dehnel et al., J. Org. Chem., 53, pp. 1566–1567 (1988).
G. M. Rozen, J. Med. Chem., 31, pp. 428–432 (1988).

Primary Examiner—David B. Springer

[57] ABSTRACT

Derivatives of 3,5-substituted pyrroline N-oxides having substituents in the 4-position have been prepared, with the 4-position substituents being selected from certain ester, polyether, and alkanoyl groups, the latter having components which bind to biological substrates. These specific derivatives are effective as spin traps for different types of free radicals to form persistent nitroxide adducts of extended half life. These adducts can be characterized by ESR spectrometry technique and provide information e.g. concerning the identification of free radicals.

10 Claims, No Drawings

PYRROLINE N-OXIDE DERIVATIVES

Pyrroline N-oxides are effective spin traps for the trapping of free radicals to facilitate their detection and study by electron spin resonance (ESR) spectroscopy techniques. A spin trap is a diamagnetic compound that reacts with a transient free radical to produce a more stable adduct. This adduct gives rise to an ESR signal which allows identification of the original free radical through parameters including hyperfine coupling constants and g-values.

This invention is directed to substituted pyrroline N-oxide derivatives and their preparation. With alkyl groups at the 3- and 5-positions of pyrroline N-oxide, it has been found possible to introduce different substituents in the 4-position. One of the 3,5-alkyl groups may be phenyl. These derivatives with different substituents at the 4-position are advantageous over spin traps with alkyl substituents present only in the 3- and 5-positions of pyrroline N-oxide, due to the flexibility to introduce a wide variety of functional groups at the 4-position; for example:

(a) attachment of a group to enhance the specificity for specific free radicals
(b) attachment of a polar group to enhance the solubility of a spin trap in water;
(c) attachment of a specific group that provides a strong binding affinity to biological substrates in order to facilitate in vivo trapping studies.

BACKGROUND AND PRIOR ART

In recent years, interest in the behaviour of free radicals in biological systems has increased. Radicals such as hydroxyl, peroxyl and superoxide radical anion have been implicated in a variety of cellular responses including aging, cancer, ischemic tissue injury and phagocytosis. Despite major efforts to study the role of free radicals in cell injury, identification of these reactive species remains a problem. The technique of spin trapping the free radicals has been used to address this difficulty. In this method, transient radicals are scavenged by appropriate nitrone or nitroso compounds to form persistent nitroxide adducts that can be identified spectroscopically. Currently used spin traps include 5,5-dimethyl-pyrroline-N-oxide ($M_2PO$,), 3,3,5,5-tetramethylpyrroline-N-oxide ($M_4PO$) and N-tert-butyl-$\alpha$-phenylnitrone (PBN).

For example see J. Org. Chem. 1988 Vol. 53, 1566–1567 A. Dehnel et al and J. Med. Chem. 1988, Vol. 31, 428–432 G. M. Rosen et al. These references disclose the preparation and spin trapping properties of 3,3-dimethyl-5,5-disubstituted-4-carbethoxypyrroline N-oxide; 3,3,5,5-tetramethyl pyrroline N-oxide and 3,3'-diethyl-5,5-dimethylpyrroline-N-oxide. These compounds are effective spin traps or scavengers for free radicals such as t-BuO*, *$CH_2OH$, *OH and Ph* with the half-lives of the adducts being several hours; however poor selectivity as well as poor solubility in water are evident.

It would be desirable to design other derivatives of pyrroline N-oxide having improved, additional and/or more selective spin trapping properties. We have prepared derivatives having other selected substituents in the 4-position, these substituents bestowing properties from among: extended adduct half life, enhanced selectivity toward specific free radicals, ability to bind to a wide variety of proteins, or other biological substrate and enhanced solubility in aqueous media.

SUMMARY OF THE INVENTION

The following derivatives have been prepared as part of the invention:
substituted pyrroline N-oxides having the formula

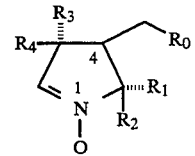

where $R_0$ is selected from the group consisting of
(1) ester —$R_5$—CO—O—$R_6$ where $R_5$ is an alkylene group of 1–6 C atoms and $R_6$ is an alkyl group of 1–4 C atoms;
(2) polyether —O—[$R_7$—O]$_x$—$R_8$ where $R_7$ is an alkylene group of 1–3 C atoms, $R_8$ is an alkyl group of 1–2 C atoms, and X is 1–4;
(3) substituted alkanoyl —O—CO—$R_9$—y where $R_9$ is an alkyene group of 1–6 C atoms, and Y is a group having an affinity for or binding to, a biological substrate;

and where $R_1$, $R_2$, $R_3$, and $R_4$ are alkyl, deuterated alkyl or cyclic alkyl groups of up to 6 C atoms, or phenyl groups; with the proviso that only up to one of the $R_1$–$R_4$ groups may be phenyl.

Illustrative compounds include the 4-[2-(ethoxycarboxyl)ethyl]-, the 4-(methoxymethoxymethyl)-, the 4-(methoxyethoxymethoxymethyl)-, the 4-(N-malimidobutyryloxymethyl) and the 4-biotinyl-derivatives.

The invention includes the process of preparing substituted pyrroline N-oxides comprising:
(a) providing a pyrrolidine compound of the formula

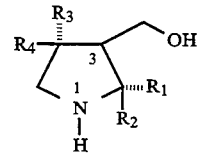

where $R_1$–$R_4$ are alkyl, cyclic alkyl or phenyl, and protecting the amine N with a protecting group;
(b) conducting one step from
 (i) reacting this 3-hydroxymethyl-N-protected compound with one of the group consisting of halogenated ethers including polyethers, and carboxylic acids, to form an ether- or ester-linked substituent; and
 (ii) oxidizing the 3-hydroxymethyl group to the corresponding aldehyde and reacting the 3-aldehyde with a phosphorane alkenyl carboxylate via a Witting reacting to attach a carboxylate substituent; and
(c) removing the N-protecting group, and oxidizing to form the corresponding substituted pyrroline N-oxide.

These compounds are useful as spin traps for free radicals i.e. form adducts with short-lived free radicals, the adducts having a longer life allowing detailed characterization and observation. The compounds can be chosen to have the capability to bind to proteins and other biological substrates.

DETAILED DESCRIPTION

The pyrroline N-oxide spin traps function by having a charge distribution and steric configuration between the N-oxide and the 2-position favourable for attracting and retaining various free radicals as adducts. Substituents in the 3- and 5-positions serve the function of bestowing a limited increase in adduct lifetime but have no effect on the selectivity. Recent tests have indicated that substituents in the 4-position have a further effect on adduct formation and stability as well as on the selectivity. In the course of investigating this further effect, we have prepared various 4-substituted derivatives.

The first type of compound investigated was one having a carboxylic acid ester group spaced from the pyrroline C-4 ring carbon by at least two carbon atoms. It was found possible to prepare this type by starting with the 4-carbethoxypyrroline, reducing to form the 3-(hydroxymethyl) pyrrolidine, selectively protecting the amine group e.g. with benzyl formate (CBz group), oxidizing sufficiently to form the 3-aldehyde (3-formal), reacting with a phosphorane alkenoate (Witting reaction) to introduce an alkenoate group on the aldehyde carbon, hydrogenating the alkene double bond and removing the protecting group, and reoxidizing to form the pyrroline-N-oxide. This process is illustrated in Example 1.

Suitable reducing agents to form the 3-hydroxymethylpyrrolidine include lithium aluminum hydride and its equivalents and the protecting groups for the pyrrolidine (secondary amine) include benzyl formyl, and alkyl formyl. Oxidizing to form the 3-aldehyde-pyrrolidine can be carried out by mild oxidizing agents such as pyridinium chlorochromate (PCC) or under Swern oxidation conditions. Hydrogenation to reform the free amine can be conducted using Pd over carbon (5 or 10%) or alternatively the blocking group can be removed under mild acidic conditions. The oxidation to reform the nitrone or pyrroline N-oxide can be carried out using hydrogen peroxide with sodium tungstate as a catalyst or using Davis reagent. Davis reagent (2-(phenylsulfonyl)-3-aryloxaziridine) may be needed to facilitate the oxidation in some cases (see Examples 3 and 4). Still other oxidation systems could be used.

The 4-carbethoxypyrroline starting compound can have various alkyl (1–6 C atoms), cyclic alkyl (3–8 membered ring) or phenyl groups in the 3- and 5-positions, with the proviso that no more than one substituent can be phenyl. The carboxylic ester group can be spaced from the C-4 carbon by from 2 to 7 C atoms (achieved by varying the Wittig reagent). The esterifying group can be an alkyl group of from 1–4 C atoms (again by adjusting the Wittig reagent).

The second type of compound investigated was that having a polyether chain in the 4-position. The preparation proceeds similarly to that for type one as far as the 3-hydroxymethyl-N-protected-pyrrolidine. The 3-hydroxymethyl group then is condensed with a halogenated ether (or polyether) to form a di- or poly-ether chain. The 3-polyether-pyrrolidine then is hydrogenated and oxidized to re-form the pyrroline N-oxide as before. This second type is illustrated in Example 2.

The halogenated ether reactant usually will have the halogen on one of the end C atoms but this is not essential. The halogen may be chlorine, bromine or iodine. The internal alkylene groups in the polyether chain may be the same or different and have up to 3 C atoms and there may be up to 4 such groups. The end alkyl group usually will be methyl or ethyl. The condensation with the halogenated ether may be carried out in dichloromethane or in tetrahydrofuran (THF) in the presence of diisopropylamine at room temperature. Other suitable reagents such as triethylamine or sodium hydride could also be used.

The third type of compound is one having the 4-position substituent (substituted alkanoyl) coupled by an esterification reaction to the 4-hydroxymethyl group. Examples are 4-(N-malimidobutyryloxymethyl)-3,3,5,5-tetramethylpyrroline N-oxide (see Example 3) and 4-(O-biotinoxymethyl)-3,3,5,5-tetramethylpyrroline N-oxide (see Example 4). Compounds having a an esterifyable alkanoic carboxylic group, spaced from the binding group are esterified by the 3-hydroxymethyl group on the N-protected pyrrolidine and the coupled product converted to the corresponding pyrroline-N-oxide as before. In this third type, in the 4-position substituent the space between the carboxylic acid group and the substrate binding group can be that of an alkylene group of from 1–6 C atoms. In general, the alkanoyl-binding group substituent has the formula —O—CO—$R_9$—Y where $R_9$ is an alkylene group of 1–6 C atoms, and Y is a group having an affinity for, or binding to, a biological substrate.

The biotin and N-malimidobutyric acid used in Examples 3 and 4 are available commercially. Other N-malimidoalkanoic acids can be prepared by known techniques, the alkanoic acid having from 2–7 C atoms.

We have found it preferable to activate the carboxylic acid group of this third type to render it in the form of an active ester as shown in scheme 3 and 4. These forms are found to be more reactive with the 3-hydroxymethylpyrrolidine and can lead to increased yields. Suitable activation procedures are described in Examples 3 and 4. Alternative ways of making such active esters are using dicyclohexylcarbodiimide (DCC) or N-hydroxysuccinic anhydride or carbonyldiimidazole to activate the carboxyl group.

In general, the preparation process may be summarized as follows:

(a) providing a pyrrolidine compound of the formula

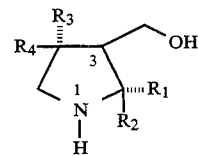

where $R_1$–$R_4$ are alkyl, cyclic alkyl or phenyl, and protecting the amine N with a protecting group;

(b) conducting one step from
(i) reacting this 3-hydroxymethyl N-protected compound with one of the group consisting of halogenated ethers including polyethers, and carboxylic acids, to form an ether- or ester-linked substituent; and
(ii) oxidizing the 3-hydroxymethyl group to the corresponding aldehyde and reacting the 3-aldehyde with a phosphorane alkenyl carboxylate via a Wittig reaction to attach a carboxylate substituent; and (c) removing the N-protecting group, and oxidizing to form the corresponding substituted pyrroline N-oxide.

Each of these 3 types of compounds are useful as spin traps for free radicals. The first type, having a carboxylate group remote from the ring has a specificity for the hydroxyl free radical, and extended half-life of the adduct (the adduct has stability in a superoxide flux). The second type, having a polyether chain, has general properties of trapping free radicals, and some enhancement of water solubility. The polyether chain has good stability in alkaline media: however these chains are very sensitive to mild acidic conditions to provide the free hydroxyl group again.

In recent years, interest in the knowledge of free radicals in biological systems has increased. Reactive intermediates such as hydroxyl and superoxide radical anion have been proposed to mediate a variety of cellular responses including cancer. Despite efforts to study the role of free radicals in cell injury, the biggest common hurdle is the identification of these reactive species. The technique of spin trapping has been used to address this difficulty. However, the use of the trapping technique in biological systems has not been explored to its full potential due to the limited variety of available spin traps.

The third type i.e. the alkanoyl with remote binding group (e.g. malimido and biotin) has the properties of binding to biological substrates especially a wide variety of proteins as well as to certain specific proteins e.g. avidin and streptavidin. Spin traps with a malimido group can covalently bind to proteins containing cysteine amino acids using a sulphydryl group of the amino acid; whereas biotinylated spin traps have a specificity towards specific proteins such as avidin and streptavidin due to the strong binding affinity of biotin for these two proteins. This binding means that the microsite of free radicals initiation in vivo can be pin-pointed in many cases.

The following Examples are illustrative.

EXAMPLE 1

4-[Ethoxycarbonyl)ethyl]-3,3,5,5-tetramethyl-1-pyrroline N-oxide(7)

The starting compound 3,3,5,5-tetramethyl-4-carbethoxy-1-pyrroline (1) was prepared as outlined in the A. Dehnel et al 1988 reference given above (see IVa in Scheme I therein).

To a mixture of lithium aluminum hydride (LAH, 0.8 g, 20.0 mmol) in ether (10 mL) was added dropwise a solution of this 4-carbethoxy pyrroline compound (1, 4.95 g, 25.12 mmol) in ether (100 mL), over a period of three h. After the addition was completed, the mixture was refluxed for 1 h. It was then quenched by careful dropwise addition of 1/1 solution of 10% NaOH and 95% ethanol. The organic layer was separated, dried and evaporated to dryness. Crystallization in 95% ethanol gave 3-Hydroxymethyl-2,2,4,4-tetramethyl-1-pyrrolidine (2, 3.8 g, 97%) as white crystals.

To a mixture of 2 (4.7 g, 30.0 mmol and $K_2CO_3$ (4.8 g, 35.0 mmol) in acetonitrile (100 mL) was added a solution of benzyl chloroformate (4.7 mL, 33 mmol) in acetonitrile (15 mL). After stirring at $-20°$ C. for 2.5 h, the mixture was brought to 25° C., quenched with a phosphate buffer solution (20 mL) and extracted with dichloromethane (200 mL). The combined organic phase was dried and evaporated. The oily residue was purified by flash chromatography over silica gel and eluted with 1:3 ethyl acetate:hexane to give 8.2 g of N-benzyloxycarbonyl-3-hydroxymethyl-2,2,4,4-tetramethyl-pyrrolidine (3, 92%) as a white solid.

To a solution of 3 (2.9 g, 10.0 mmol) in dichloromethane was added pyridinium chlorochromate (PCC, 3.2 g) at room temperature and the mixture stirred for 3 h. The corresponding 3-aldehyde compound 4 was obtained in 93% yield.

When aldehyde compound 4(2.9 g, 10.0 mmol) dissolved in benzene (30 mL) was subjected to Wittig reaction conditions by warming to 55°-60° C. in the presence of (carbethoxymethylene)triphenylphosphorane (5.2 g, 15.0 mmol), the unsaturated ester derivative 5 was obtained in 76% yield.

A solution of the unsaturated ester 5 (3.6 g, 10 mmol) in 95% ethanol (35 mL) and 10% palladium on charcoal (200 mg) was hydrogenated with $H_2$ at atmospheric pressure for 10 h. The mixture was filtered through Celite ® 545 (5 g) and the solvent evaporated to give 2.1 g of the N-deprotected pyrrolidine 6 (free amine). This latter compound then was oxidized to the nitrone as follows.

To a stirred solution of 6 (1.13 g, 5.0 mmol) and $Na_2WO_4.2H_2O$ (0.82 g, 20 mmol in methanol (25 mL) was added dropwise hydrogen peroxide 33% (2 mL) at 0° C. After stirring at 0° C. for 4 h the solvent was evaporated and the residue taken up with dichloromethane (50 mL), washed with brine (10 mL), dried and evaporated to dryness. The residue was purified by flash chromatography over silica gel and eluted with 20:1 dichloromethane:methanol to give 7 (85%) as a yellow oil.

Similarly the same steps were repeated with 5,5-bis(-deuteriomethyl)-3,3-dimethyl-4-carbethoxypyrroline to give the same compound 7 except having two —$CD_3$ groups at the C-5 position.

By using other phosphorane esters in the Wittig reaction, the number of carbon atoms between the carboxyl ester and the C-4 ring carbon can be varied from 2 carbons e.g. to 6 C atoms. The synthesis is summarized in scheme 1.

SCHEME 1

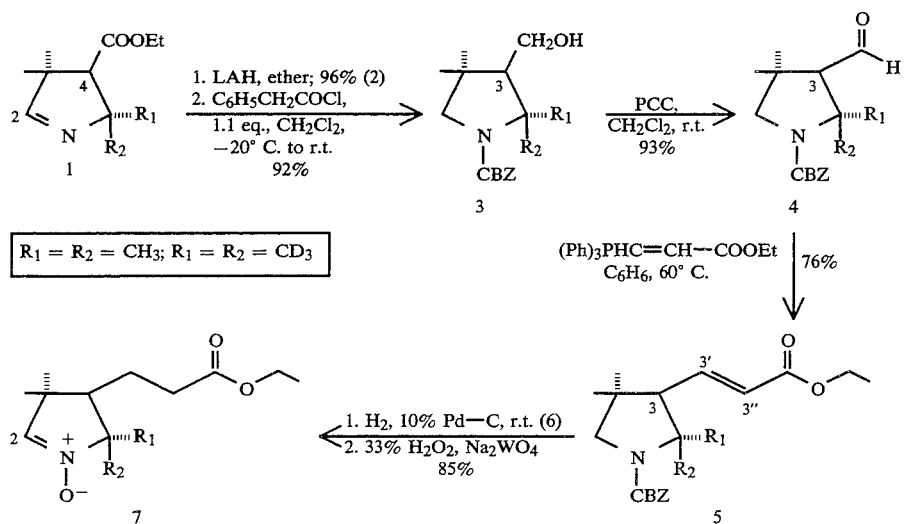

EXAMPLE 2

4-(Methoxymethoxymethyl)-3,3,5,5-tetramethyl-1-pyrroline N-oxide(10)

The N-protected 3-hydroxymethylpyrrolidine (3) was prepared as in Example 1. To a solution of 3 (1.45 g, 5.0 mmol) in dichloromethane (50 mL) was added diisopropylamine (1.29 g, 10 mmol) dropwise at 25° C. It was followed by a dropwise addition of a solution of methoxymethylchloride (9.55 g, 6.0 mmol) in dichloromethane (10 mL). After stirring at 25° C. for 2 h, it was diluted with dichloromethane (200 mL) and buffer solution (pH 7, 25 mL). The organic layer was collected, dried over MgSO4 and evaporated. The resulting solid residue was purified by flash chromatography over silica gel and eluted with 1:5 ethylacetatehexane to give 8 (1.35 g, 81%) as a white solid.

A solution of 8 (10.0 mmol) in 95% ethanol (50 mL) and palladium on charcoal (10%, 200 mg) was hydrogenated under atmospheric pressure for 10 h. The mixture was filtered over Celite ® 545 (5 g) and the solvent was evaporated to give 9 in 95% yield as a colourless oil.

To a stirred solution of 9 (5.0 mmol) and Na2WO4×2H2O (5.0 mmol %) in methanol (25 mL) was added dropwise hydrogen peroxide 33% (15.0 mmol) at 0° C. After stirring at 0° C. for 4 h, the solvent was evaporated to dryness. The solid residue was taken up with dichloromethane (50 mL), washed with brine (10 mL), dried and evaporated to dryness. The residue was purified by flash chromathography over silica gel and eluted with 20:1 dichloromethane:methanol to give 10 4-(methoxymethoxymethyl)-3,3,5,5-tetramethyl-1-pyrroline N-oxide. The procedure is summarized in scheme 2A.

SCHEME 2A

-continued
SCHEME 2A

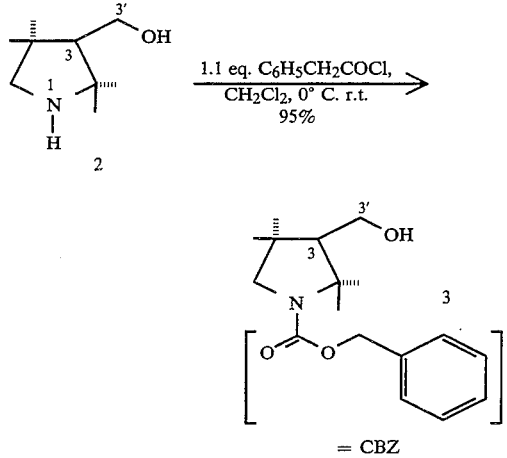

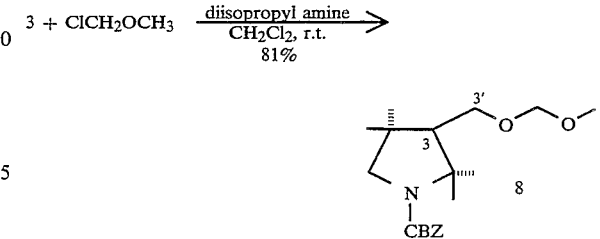

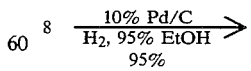

-continued
SCHEME 2A

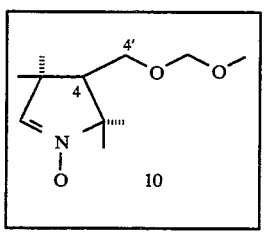

4-(Methoxyethoxymethoxymethyl)-3,3,5,5-tetramethyl-1-pyrroline N-Oxide (13)

To a solution of 3 (1.45 g, 5.0 mmol) in dichloromethane (50 mL) was added diisopropylamine (1.29 g, 10 mmol) dropwise at 25° C. It was followed by a dropwise solution of methoxyethoxymethylchloride (0.74 g, 6.0 mmol) in dichloromethane (10 mL). After stirring at 25° C. for 32 h, the solution was diluted with dichloromethane (200 mL) and pH7 buffer solution (25 mL). The organic layer was collected, dried over $MgSO_4$ and evaporated. The resulting solid residue was purified by flash chromatography over silica gel and eluted with 1:5 ethylacetate:hexane to give 11 (75%) as a white solid.

A solution of 11 (10.0 mmol) in 95% ethanol (50 mL) and palladium on charcoal (10%, 200 mg) was hydrogenated under atmospheric pressure for 10 h. The mixture was filtered over Celite ® 545 (5 g) and the solvent was evaporated to give 12 in 93% yield as a white oil.

To a stirred solution of 12 (5.0 mmol) and $Na_2WO_4 \times 2H_2O$ (5.0 mmol%) in methanol (25 mL) was added dropwise hydrogen peroxide 33% (15.0 mmol) at 0° C. After stirring at 0° C. for 4 h, the solvent was evaporated to dryness. The solid residue was taken up with dichloromethane (50 mL), washed with brine (10 mL), dried and evaporated to dryness. The residue was purified by flash chromathography over silica gel and eluted with 20:1 dichloromethane:methanol to give 13 in 80% yield as a yellow oil. This preparation is summarized in scheme 2B.

SCHEME 2B

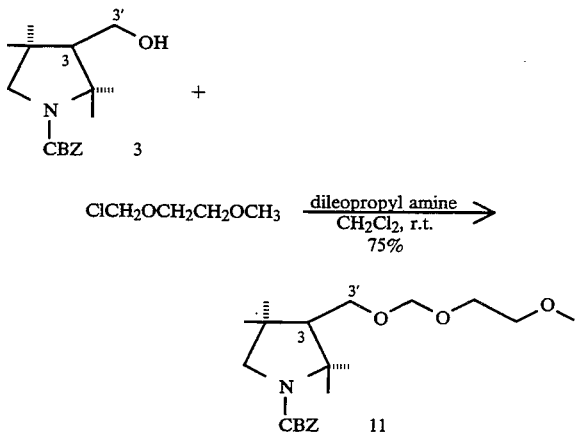

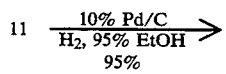

-continued
SCHEME 2B

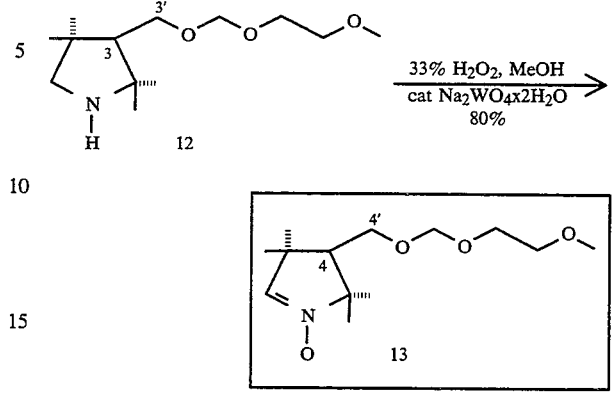

By varying the chloroether reagent, it is possible to introduce other polyether groups in the 4-position.

EXAMPLE 3

4-(N-Malimidobutyryloxymethyl)-3,3,5,5-tetramethyl-pyrroline-N-oxide (17)

Compound 3 from example 1 was used as starting material to couple with N-malimidobutyric acid after activation. Two alternative activation/coupling procedures are illustrated.

Procedure (a) Activation of carboxyl group of N-malimidobutyric acid: A solution of N-malimidobutyric acid (14, 0.001 mol, 0.183 g) and $SOCl_2$ (0.002 mol, 0.238 g) in benzene (15 mL) was warmed at 70° C. for 2 h. The solvent was evaporated in vacuo and the residue collected was used directly for the next step.

Coupling:

The residue dissolved in 3 ml of THF and added dropwise to a solution of 3 (0.001 mol, 0.291 g), $Et_3N$ (0.0015 mol, 0.2 mL) and 4-dimethylaminopyridine (DMAP, 2 mol %) in THF (15 mL) under argon. The solution was further stirred at 55° C. for 3 h. The reaction mixture was diluted with $CH_2Cl_2$ (50 mL) and quenched with $NH_4Cl$ solution. The organic layer was separated, dried and evaporated in vacuo. The residue was flash chromatographed (elution with ethyl acetate:-Hexane, 1:3) to give N(benzyloxycarbonyl)-3-(N-malimidobutyryloxymethyl)-2,2,4,4-tetramethyl-pyrrolidine (15, 0.237 g, 52%).

Procedure (b) Activation of carboxyl group of N-malimidobutyric acid: To a solution of N-malimidobutyric acid (14, 0.0024 mol, 0.439 g) and $Et_3N$ (0.003 mol, 0.4 mL) in THF (25 mL), under argon, added dropwise freshly prepared 2,4,6-trichlorobenzoyl chloride (0.0024 mol, 0.583 g) in THF (15 mL) at room temperature. The mixture was stirred for 1.5 h. $Et_3N$·HCl was filtered and the mother liquor was directly used for the coupling reaction.

Coupling:

The liquor was added to a solution of 3 (0.002 mol, 0.582 g), DMAP (0.0022 mol, 0.268 g) in THF (20 mL) under argon. The solution was stirred at room temperature for 30 minutes. The reaction mixture diluted with $CH_2Cl_2$ (100 mL) and quenched with an addition of pH 7 buffer solution (10 mL). The organic layer was collected, dried over $MgSO_4$ and evaporated in vacuo. The residue was flash chromatographed (elution with EtOAc:Hexane, 1:3) to give 15 (0.848 g, 93%).

30% HBr in Acetic acid (1.0 ml) was added dropwise to a solution of 15 (0.001 mol) in CH$_2$Cl$_2$ (5 mL) at room temperature. After 15 minutes, the reaction was quenched with 10% Na$_2$CO$_3$ solution. The organic layer was collected, dried over MgSO$_4$ and evaporated in vacuo. The residue was flash chromatographed (elution with CH$_2$Cl$_2$:MeOH, 40:3) to give 16 (0.276 g, 85%).

Freshly prepared Davis' reagent (0.0022 mol, 0.574 g) was added to a solution of 16 (0.01 mol, 0.322 g) in THF (15 mL). The solution was stirred at room temperature for 20 minutes. The residue obtained was filtered and the solvent was collected and evaporated in vacuo. The residue was flash chromatographed (elution with CH$_2$Cl$_2$:MeOH, 40:1.5) to give 17 (0.292 g, 87%). This preparation is summarized in scheme 3.

SCHEME 3

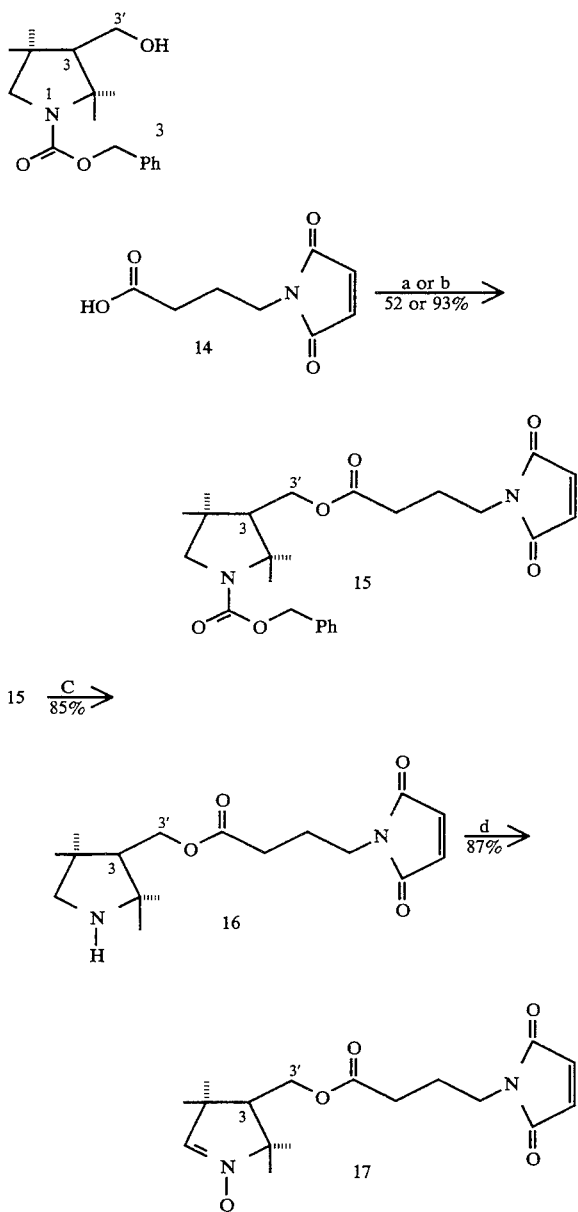

-continued
SCHEME 3

(a) SOCl$_2$, 55° C.;
(b) 2,4,6-trichlorobenzoyl chloride, THF, rt, 30 min;
(c) 33% HBr in AcOH, 15 min;
(d) 2.2 eq 2-(phenylsulphonyl)-3-phenyloxaziridine {Davis' Reagent}, THF, rt, 20 min

EXAMPLE 4

4-biotinyl-3,3,5,5-tetramethyl-1-pyrroline N-oxide (21)

3-hydroxymethyl-N-(benzyloxycarbonyl)-2,2,4,4-tetramethyl-1-pyrrolidine (compound 3 from Example 1) was used as starting material to couple with biotin after biotin activation.

Activation of carboxyl group of biotin: To a solution of biotin (18, 0.002 mol, 0.488 g) and Et$_3$N (0.003 mol, 0.4 mL) in dimethylformamide (DMF) (15 mL), under argon, was added dropwise freshly prepared 2,4,6-trichlorobenzoyl chloride (0.002 mol, 0.486 g) in DMF(5 mL) at 37°–40° C. The mixture was stirred for 1.5 h. It was directly used for the coupling step.

Coupling:

To the above solution was added compound 3 (0.002 mol), and DMAP (0.003 mol) under argon. The mixture was stirred at 40°–45° C. for 1.5 h. The reaction mixture was diluted with CH$_2$Cl$_2$ (100 mL) and quenched with pH7 buffer solution (20 mL). The organic layer was collected, dried over MgSO$_4$ and evaporated in vacuo. The residue was flash chromatographed (elution with CH$_2$Cl$_2$:MeOH, 30:1) to give 19 (0.672 g, 65% and 93%) based on recovered starting material.

Trimethylsilyliodide (0.002 mol, 0.4 g) was added dropwise to a solution of 19 (0.001 mol, 0.517 g) in CH$_3$CN at room temperature. After 20 minutes, the reaction was quenched with 10% Na$_2$CO$_3$ solution. The organic layer was collected, dried over MgSO$_4$ and evaporated in vacuo. The residue was flash chromatographed (elution with CH$_2$Cl$_2$:MeOH, 10:1) to give 20 (0.31 g, 81%).

Freshly prepared Davis reagent (0.0035 mol, 0.9135 g) was added to a solution of 20 (0.001 mol, 0.383 g) in THF (15 mL). The solution was stirred at room temperature for 20 minutes. The residue obtained was filtered and the solvent was collected and evaporated in vacuo. The residue was flash chromatographed (elution with CH$_2$Cl$_2$:MeOH, 10:1) to give 21 (0.351 g, 85%). This preparation is summarized in scheme 4.

During this formation of the nitrone 21 from free amine 20 the sulfide group of biotin was oxidized to sulphoxide. A milder oxidation would avoid forming the sulphoxide: however the sulphoxide is not detrimental. Both the biotin and oxidized biotin bind to avidin and streptavidin.

SCHEME 4

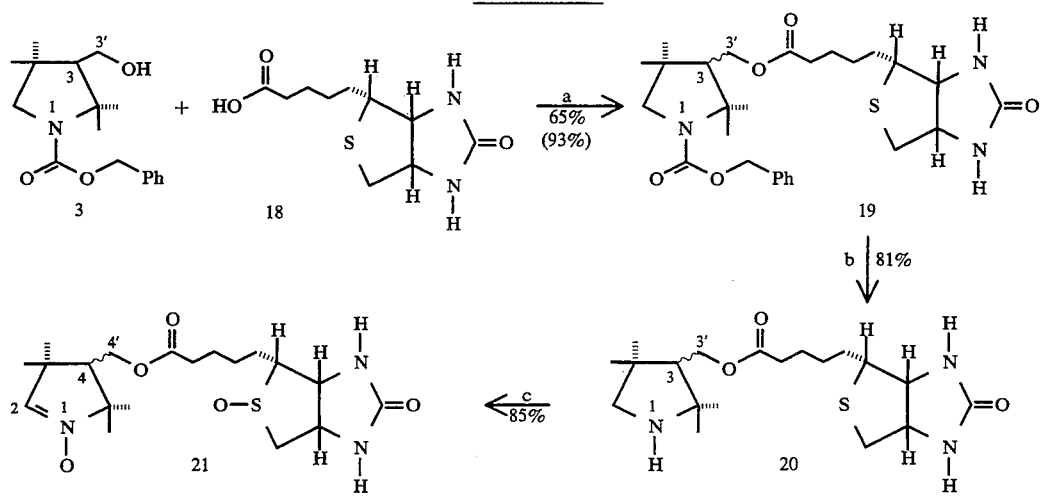

(a) 2,4,6-trichlorobenzoyl chloride, DMF, 55° C., 90 min;
(b) 2.0 eq TMSI, CH3CN, 15 min;
(c) 3.5 eq 2-(phenylsulphonyl)-3-phenyloxaziridine {Davis' Reagent}, THF-DMF, rt, 20 min.

The embodiments of the invention in which an exclusive property or privilege is claimed are defined as follows:

1. Substituted pyrroline N-oxides having the formula

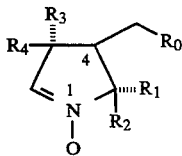

where $R_0$ is selected from the group consisting of
   (1) ester $-R_5-CO-O-R_6$ where $R_5$ is an alkylene group of 1-6 C atoms and $R_6$ is an alkyl group of 1-4 C atoms;
   (2) polyether $-O-[R_7-O]_x-R_8$ where $R_7$ is an alkylene group of 1-3 C atoms, $R_8$ is an alkyl group of 1-2 C atoms, and X is 1-4;
   (3) substituted alkanoyl $-O-CO-R_9-Y$ where $R_9$ is an alkylene group of 1-6 C atoms, and Y is a group selected from malimido or biotin;

and where $R_1$, $R_2$, $R_3$, and $R_4$ are alkyl, deuterated alkyl or cyclic alkyl groups of up to 8 C atoms, or phenyl groups; with the proviso that only up to one of the $R_1$-$R_4$ groups may be phenyl.

2. The N-oxide of claim 1 wherein $R_0$ is an ester $-R_5-CO-O-R_6$ wherein both $R_5$ and $R_6$ have 1-2 C atoms.

3. The N-oxide of claim 2 wherein $R_0$ is an ethoxycarbonyl-methyl group.

4. The N-oxide of claim 1 wherein $R_0$ is a polyether with 4-8 carbon atoms.

5. The N-oxide of claim 4 wherein $R_0$ is the dioxobutyl ether group.

6. The N-oxide of claim 1 wherein the $R_0$ is the biotinyl group.

7. The N-oxide of claim 1 wherein $R_0$ is a malimido alkanoyl moiety.

8. The N-oxide of claim 7 wherein $R_9$ has 3 C atoms and the moiety is omega-malimido-butanoyl.

9. The N-oxide of claim 1 wherein one of $R_1$-$R_4$ is a phenyl group.

10. The N-oxide of claim 1 wherein $R_1$-$R_4$ are methyl groups or deuterated methyl groups.

* * * * *